United States Patent [19]

Eggl et al.

[11] Patent Number: 5,331,398
[45] Date of Patent: Jul. 19, 1994

[54] APPARATUS FOR PHOTOMETRIC ANALYSIS

[75] Inventors: Wilfried Eggl; Rolf Amelung, both of Lemgo, Fed. Rep. of Germany

[73] Assignee: Heinrich Amelung GmbH, Lemgo, Fed. Rep. of Germany

[21] Appl. No.: 869,791

[22] Filed: Apr. 16, 1992

[30] Foreign Application Priority Data

Apr. 24, 1991 [DE] Fed. Rep. of Germany ....... 4113330

[51] Int. Cl.⁵ ................. G01N 21/13; G01N 35/00
[52] U.S. Cl. .................................................... 356/246
[58] Field of Search ............. 356/244, 246, 440, 39; 221/66, 303

[56] References Cited

U.S. PATENT DOCUMENTS

| | | | |
|---|---|---|---|
| 3,809,287 | 5/1974 | Muller-Scherak | 221/66 |
| 4,406,547 | 9/1983 | Aihara | 356/414 |
| 4,640,617 | 2/1987 | Hughes et al. | 356/244 |

*Primary Examiner*—Richard A. Rosenberger
*Attorney, Agent, or Firm*—Feiereisen & Kueffner

[57] ABSTRACT

Apparatus for photometric analysis of the coagulation behavior of blood, blood plasma or like fluids includes a cuvette container with at least one receptacle for receiving a cuvette, with the receptacle having a lower end provided with a discharge opening which is downwardly continued by a well. Arranged in the receptacle is a leaf spring for retaining the cuvette in position during photometric analysis. After photometric measurement a further cuvette is inserted in the receptacle, with the previous cuvette being simultaneously ejected.

12 Claims, 2 Drawing Sheets

APPARATUS FOR PHOTOMETRIC ANALYSIS

BACKGROUND OF THE INVENTION

The present invention refers to an apparatus for photometric analysis of coagulation behavior of blood, blood plasma or like fluids, and in particular to a cuvette container for holding a plurality of cuvettes which contain test samples for photometric measurement.

For photometric analysis of the coagulation behavior of blood or blood plasma or like fluids, it is generally known to use a cuvette container which is provided with a plurality of holding members adapted for receiving cuvettes which are of transparent material and contain a test sample. Suitably, the holding members have a cross section which corresponds to the usually rectangular cross section of the cuvettes. The photometric measurement is carried out by a photometer which includes a transmitter in form of a light source arranged in proximity of one narrow side of the cuvettes and a receiver in form of a light detector located in proximity of the other opposing narrow side of the cuvettes.

After completing the photometric analysis, the cuvettes are generally pulled out of the holding member, either manually, which is less desirable because of the obvious risk of contacting the cuvette content, or through suitable supply and discharge mechanisms by which the cuvettes are automatically fed and removed from the pertaining holding members. Regardless as to whether the removal is done manually or automatically, a withdrawal of the cuvettes requires an additional working step which usually takes a relatively long period so that extended pauses are experienced between successive photometric measurements. In particular, in case of analyzing a large number of test samples, as generally encountered in medical laboratories, the occurrence of such extended pauses is disadvantageous as it impedes an optimal utilization of the apparatus. Such drawbacks are compounded when using particular means such as gripper arms for automatically withdrawing the cuvettes because the gripper arm after picking up the cuvette has to travel back to an appropriate position for depositing the cuvette. This adds further to the actual discharge period.

U.S. Pat. No. 4,406,547 describes an apparatus for effecting photometric measurements by using a turntable which holds a number of cuvettes and rotates step by step for positioning the cuvettes for subsequent photometric measurement. Each cuvette is of particular design and includes at its upper periphery a supporting flange by which the cuvette is retained in position in a complementary holding member. After completing measurement, each cuvette is removed by a separate ejector which includes an L-shaped arm and a solenoid. When the solenoid is energized, the arm pulls the cuvette into an opening through which the cuvette can then fall down into a waste tank. An analyzer of this type is disadvantageous because it requires a relatively complicated ejector for removing the cuvettes, and because it is not suitable for use with conventional cuvettes; rather, the cuvettes as employed in this prior art are of particular design in order to allow proper positioning within the holding members.

SUMMARY OF THE INVENTION

It is thus an object of the present invention to provide an improved apparatus for photometric analysis obviating the afore-stated drawbacks.

In particular, it is an object of the present invention to provide an improved apparatus for photometric analysis which allows a rapid and simple removal of the cuvettes.

These objects and others which will become apparent hereinafter are attained in accordance with the present invention by providing a cuvette container which has at least one receptacle for receiving a cuvette, with the receptacle having a lower end provided with a discharge opening, and by locking the cuvette in position during photometric analysis by means of a suitable fastener.

Through the provision of such a cuvette container, the cuvettes, after completing the photometric measurement, can easily be discharged downwardly and ejected into a subjacent reservoir by a new cuvette which is inserted from atop. An upward withdrawal is eliminated so that no time is wasted for removal of the cuvette, thus considerably shortening the cycle for photometric measurement. Suitably, the cuvettes have corresponding bottom dimensions and top dimensions in order to prevent superimposed cuvettes from jamming or interlocking during insertion of a new cuvette and simultaneous ejection of a subjacent cuvette. Preferably, the ejected cuvette is released from the fastener before the newly inserted cuvette reaches its locked position for photometric measurement.

Preferably, a leaf spring is used as fastener by which the cuvette is urged against the opposing wall surface of the receptacle and retained through frictional engagement.

Advantageously, the cuvette container can easily be combined with an incubator for heating the test sample to a certain temperature prior to photometric measurement. The incubator may be placed upon the cuvette container and has a well which extends in elongation of the receptacle so that a cuvette can directly be pushed into the subjacent receptacle and suitably positioned for subsequent photometric measurement, while at the same time a cuvette which is disposed in the receptacle is ejected.

BRIEF DESCRIPTION OF THE DRAWING

The above and other objects, features and advantages of the present invention will now be described in more detail with reference to the accompanying drawing in which.

DETAILED DESCRIPTION OF PREFERRED EMBODIMENTS

Figure 1:
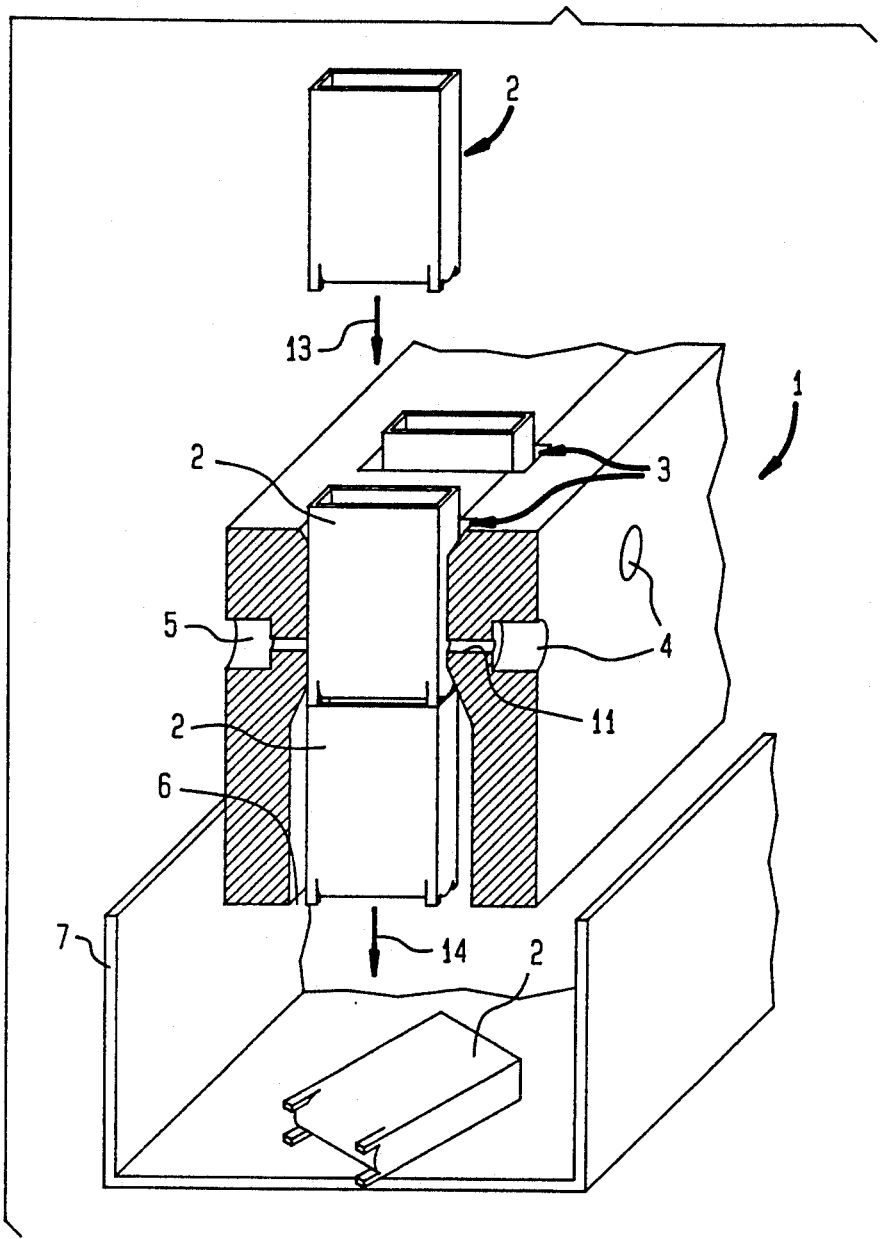
FIG. 1 is a schematic, partly sectional perspective view of one embodiment of an apparatus for photometric analysis according to the present invention.

Throughout all the Figures, the same or corresponding elements are always indicated by the same reference numerals.

Referring now to the drawing and in particular to FIG. 1, there is shown a schematic, partly sectional perspective view of one embodiment of an apparatus for photometric analysis of the coagulation behavior of blood, blood plasma or the like fluids, including a cuvette container 1 which is provided with several successively arranged slot-shaped receptacles (only two are shown), generally designated by reference numeral 3 for receiving cuvettes 2. The cuvettes 2 are made of transparent material and are of conventional parallelepiped configuration, with the receptacles 3 having matching rectangular cross section. The receptacles 3 are provided with open top for allowing insertion of cuvettes 2 and with a discharge opening at their lower end. Suitably, the upper perimeter of each receptacle 3 is bevelled to facilitate insertion of the cuvettes 2.

The supply of cuvettes 2 and introduction thereof into the receptacles 3 can be done manually or automatically by a suitable gripper which does not form part of the invention and thus has been omitted from the drawing for sake of simplicity.

As shown in FIG. 1, the discharge opening of each receptacle 3 is continued downwardly by a well 6 which has a cross section exceeding the cross sectional dimension of the cuvette 2. At the junction to the receptacle 3, the well 6 is bevelled.

Incorporated within the cuvette container 1 is a photometer which includes a transmitter in form of a plurality light sources suitably located in respective recesses or cavities 4 along one narrow side of the receptacle 3, and a receiver in form of a plurality of light detectors which are located in respective recesses or cavities 5 along the opposing narrow side of the receptacle 3. Light emitting from each light source is guided through a channel 11 through the cuvette 2 and received by the opposing light detector. Evidently, the number of light sources and light detectors corresponds to the number of receptacles 3.

It will be appreciated by persons skilled in the art that the photometer is not part of the invention, and therefore not shown in detail in the drawing. Also, the photometer must contain much additional apparatus which does not appear in the foregoing Figure as it is not part of the invention.

Arranged below the cuvette container 1 is a reservoir 7 by which ejected waste cuvettes 2 are collected. The reservoir 7 may be detachably secured to the cuvette container 1 and may be of any suitable design to facilitate removal from the apparatus and subsequent disposal of the cuvettes 2.

Figure 2:
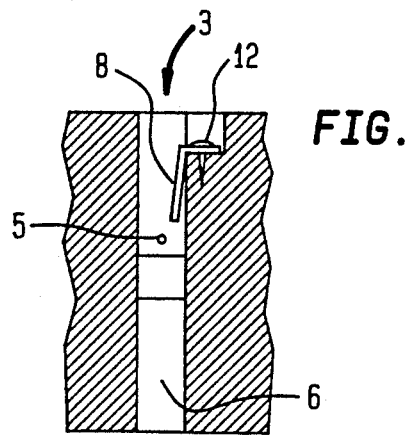
FIG. 2 is a fragmentary longitudinal section of a cuvette container showing a manner by which a cuvette retained in position within a cuvette receptacle.

Turning now to FIG. 2, there is shown a fragmentary longitudinal section of the cuvette container 1 illustrating a manner by which a cuvette 2 is held in position within the receptacle 3. As can be seen from FIG. 2, a fastener or retainer in form of a leaf spring 8 is suitably mounted at the broad side of the receptacle 3, e.g. by means of a nail of rivet 12. The leaf spring 8 projects into the interior of the receptacle 3 so as to urge a cuvette 2, which has been inserted into the receptacle 3, towards the opposing inside wall surface of the receptacle 3 to lock the cuvette 2 in a proper position through frictional engagement for subsequent photometric measurement.

After completing the photometric measurement of a test sample within a cuvette 2, a further cuvette 2 is inserted from above into the respective receptacle 3, as indicated by arrow 13, with the previously positioned cuvette 2 being ejected into the well 6 and into the reservoir 7 as indicated by the arrow 14 (FIG. 1). The leaf spring 8 is biased in such a manner that a retained cuvette 2 is released before a newly introduced cuvette 2 reaches its locked position. That means, before the new cuvette 2 occupies its proper position for photometric measurement, the preceding cuvette 2 falls already down through the well 6 into the reservoir 7.

Persons skilled in the art will understand that the use of a leaf spring is made by way of example only. It may be certainly possible to retain the cuvettes 2 within the receptacles 3 solely through frictional engagement. This requires, however, a precise match of the cross section of the receptacles 3 with the cross section of the cuvettes 2. In order to secure an unimpaired discharge of the cuvettes 2, the receptacles 3 should have a depth which is smaller than the height of the cuvettes 2.

Figure 3:
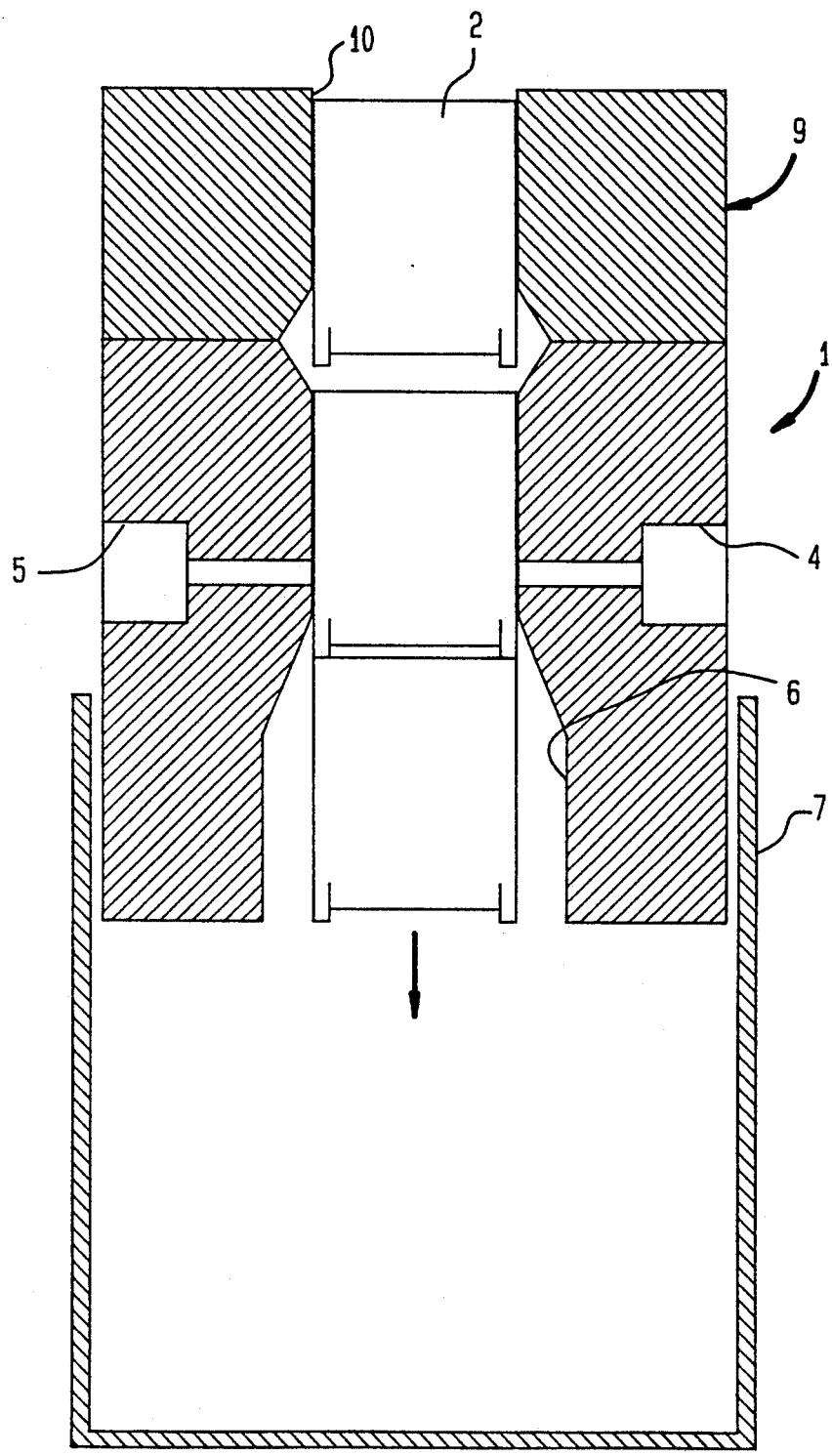
FIG. 3 is a schematic sectional view of the apparatus of FIG. 1 in combination with an exemplary incubator.

Turning now to FIG. 3, there is shown a schematic sectional view of the cuvette container 1 in cooperation with an incubator 9 by which the test samples are heated and kept at a certain temperature. Suitably, the incubator 9 is placed upon the top of the cuvette container 1 and includes wells 10 in alignment with the subjacent receptacles 3 so that each well 10 and the associated subjacent receptacle 3 have a common opening of passage. After termination of the incubation time, which is longer than the time for photometric measurement, the heated cuvette 2 is pushed into the receptacle 3 of the container 1 for subsequent photometric measurement whereby the cuvette 2 in the subjacent receptacle 3 is forced into the well 6 and into the reservoir 7. Suitably, the well 10 is also provided with retainers (not shown) for keeping the cuvette 2 in locked position.

Persons skilled in the art will understand that the incubator 9 may also be a separate unit from which respective cuvettes can be withdrawn and then inserted into the cuvette container 1. Also, the incubator 9 is shown only schematically and contains much apparatus which, however, is omitted from FIG. 3 for sake of simplicity.

While the invention has been illustrated and described as embodied in an apparatus for photometric measurement, it is not intended to be limited to the details shown since various modifications and structural changes may be made without departing in any way from the spirit of the present invention.

What is claimed as new and desired to be protected by Letters Patent is set forth in the appended claims:

1. Apparatus for photometric analysis of the coagulation behavior of blood, blood plasma or the like; comprising:
    a cuvette container having at least one receptacle for receiving a cuvette from atop, said receptacle having a lower end provided with a discharge opening and a well extending in continuation of said discharge opening and flaring out from said discharge opening so as to have a cross section exceeding the cross section of said cuvette, said cuvette having a height and said receptacle having a depth which is smaller than the height of said cuvette for facilitating a discharge of said cuvette;
    a photometric unit arranged in the area of said receptacle for analyzing a test sample in the cuvette; and
    holding means arranged in said receptacle for retaining the cuvette in position during photometric analysis.

2. Apparatus as defined in claim 1 wherein said cuvette is transparent and of rectangular cross section.

3. Apparatus as defined in claim 1 wherein said receptacle has a cross section substantially corresponding to the cross section of said cuvette.

4. Apparatus as defined in claim 1 wherein said holding means includes a leaf spring extending into said receptacle.

5. Apparatus as defined in claim 1, and further comprising a reservoir detachably secured to and extending below said cuvette container for collecting discharged cuvettes.

6. Apparatus as defined in claim 1, and further comprising an incubator arranged above said cuvette container and including a well in alignment with said receptacle, with said well and said receptacle having a common opening of passage.

7. A cuvette container adapted for incorporation of a photometer for photometric analysis of the coagulation behavior of blood, blood plasma or the like fluids; comprising:
   at least one receptacle for receiving a cuvette having a height, with the photometer being arranged in the area of said receptacle, said receptacle having a lower end provided with a discharge opening and a well extending in continuation of said discharge opening and flaring out from said discharge opening so as to have a cross section exceeding the cross section of said cuvette, said receptacle having a depth which is smaller than the height of said cuvette for facilitating a discharge of said cuvette; and
   holding means arranged in said receptacle for retaining the cuvette in position during photometric analysis.

8. A cuvette container as defined in claim 7 wherein said receptacle has a cross section substantially corresponding to the cross section of said cuvette.

9. A cuvette container as defined in claim 7 wherein said holding means includes a leaf spring extending into said receptacle.

10. A cuvette container as defined in claim 7 wherein said cuvette has a height, said receptacle having a depth which is smaller than the height of said cuvette.

11. A cuvette container as defined in claim 7, and further comprising a detachable reservoir arranged below said receptacle for collecting discharged cuvettes.

12. Apparatus for photometric analysis of test samples in respective cuvettes; comprising:
   a cuvette container having at least one receptacle for receiving a cuvette of a height, with said receptacle having a lower end provided with a discharge opening and a well extending in continuation of said discharge opening and flaring out from said discharge opening so as to have a cross section exceeding the cross section of said cuvette, said receptacle having a depth which is smaller than the height of said cuvette for facilitating a discharge of said cuvette;
   a light source arranged in a cavity at one side of said cuvette container for emitting a light beam toward the cuvette;
   a light detector arranged in a cavity at the opposing side of said cuvette container for receiving the light beam transmitted from said light source through the cuvette; and
   holding means arranged in said receptacle for retaining the cuvette in position during photometric analysis.

* * * * *